(12) United States Patent
Wang et al.

(10) Patent No.: US 9,762,581 B1
(45) Date of Patent: Sep. 12, 2017

(54) MULTIFACTOR AUTHENTICATION THROUGH WEARABLE ELECTRONIC DEVICE

(71) Applicant: STRIIV, INC., Redwood City, CA (US)

(72) Inventors: David Jonq Wang, Palo Alto, CA (US); Mark A. Ross, San Carlos, CA (US)

(73) Assignee: STRIIV, INC., Redwood City, CA (US)

( * ) Notice: Subject to any disclaimer, the term of this patent is extended or adjusted under 35 U.S.C. 154(b) by 0 days.

(21) Appl. No.: 15/099,992

(22) Filed: Apr. 15, 2016

(51) Int. Cl.

| | | |
|---|---|---|
| *H04L 29/00* | (2006.01) | |
| *H04L 29/06* | (2006.01) | |
| *H04W 12/08* | (2009.01) | |
| *H04W 12/06* | (2009.01) | |
| *G06K 9/00* | (2006.01) | |
| *G07C 9/00* | (2006.01) | |
| *A61B 5/024* | (2006.01) | |

(52) U.S. Cl.
CPC .......... *H04L 63/10* (2013.01); *A61B 5/02438* (2013.01); *G06K 9/00288* (2013.01); *G06K 9/00348* (2013.01); *G06K 9/00892* (2013.01); *G07C 9/00079* (2013.01); *H04L 63/08* (2013.01); *H04L 63/0853* (2013.01); *H04L 63/0861* (2013.01); *H04W 12/06* (2013.01); *H04W 12/08* (2013.01); *G06K 2009/00939* (2013.01)

(58) Field of Classification Search
CPC . G06F 21/03; G06F 21/04; H04L 9/32; H04L 63/08; H04L 63/10
See application file for complete search history.

(56) References Cited

U.S. PATENT DOCUMENTS

| | | | |
|---|---|---|---|
| 5,283,431 A | 2/1994 | Rhine | |
| 7,775,429 B2 | 8/2010 | Radicella et al. | |
| 8,533,815 B1* | 9/2013 | Upson | H04L 9/3226 713/168 |
| 2002/0138438 A1* | 9/2002 | Bardwell | G06F 21/32 705/51 |
| 2002/0148892 A1* | 10/2002 | Bardwell | G06F 21/32 235/380 |

(Continued)

*Primary Examiner* — Madhuri Herzog
(74) *Attorney, Agent, or Firm* — Maschoff Brennan

(57) ABSTRACT

A method to implement multifactor authentication of a user may include performing biometric authentication of a person that bears the wearable electronic device and at least one of: performing knowledge-based authentication of the person or presenting an access control token of the wearable electronic device to an access reader that performs token-based authentication of the person. Performing biometric authentication may include receiving a first biometric signal generated by a wearable electronic device and determining a person-specific biometric characteristic of the person therefrom; comparing the person-specific biometric characteristic to a user-specific biometric characteristic of the user determined from a second biometric signal generated when the wearable electronic device was born by the user; and based on the comparing, determining a confidence level that the person is the user to determine a positive or negative authentication of the person as the user.

23 Claims, 6 Drawing Sheets

(56) References Cited

U.S. PATENT DOCUMENTS

| | | | |
|---|---|---|---|
| 2006/0106605 A1* | 5/2006 | Saunders | G10L 17/04 704/246 |
| 2007/0040017 A1* | 2/2007 | Kozlay | G06K 19/07354 235/380 |
| 2012/0144468 A1 | 6/2012 | Pratt et al. | |
| 2014/0337634 A1 | 11/2014 | Starner et al. | |
| 2014/0359722 A1* | 12/2014 | Schultz | H04L 9/3231 726/5 |
| 2014/0379339 A1* | 12/2014 | Timem | G10L 17/22 704/246 |
| 2015/0035644 A1* | 2/2015 | June | G07C 11/00 340/5.61 |
| 2015/0059003 A1 | 2/2015 | Bouse | |
| 2015/0089568 A1 | 3/2015 | Sprague et al. | |
| 2015/0109124 A1 | 4/2015 | He et al. | |
| 2015/0112603 A1 | 4/2015 | Zhong | |
| 2015/0286813 A1 | 10/2015 | Jakobsson | |
| 2015/0347734 A1 | 12/2015 | Beigi | |
| 2015/0379255 A1* | 12/2015 | Konanur | G06F 21/35 726/19 |
| 2016/0034707 A1* | 2/2016 | Sahu | G06F 21/31 713/168 |
| 2016/0063503 A1 | 3/2016 | Kobres et al. | |
| 2016/0224776 A1* | 8/2016 | Leow | G06F 21/34 |

\* cited by examiner

MULTIFACTOR AUTHENTICATION THROUGH WEARABLE ELECTRONIC DEVICE

FIELD

Some embodiments described herein generally relate to multifactor authentication through a wearable electronic device.

BACKGROUND

Unless otherwise indicated herein, the materials described herein are not prior art to the claims in the present application and are not admitted to be prior art by inclusion in this section.

Many access control systems exist to control access to, e.g., property. One type of access control system uses a lock and a corresponding key. Anybody in possession of the corresponding key can insert it into the lock to gain access to the property, such as a house accessed through a door with the lock or a swimming pool accessed through a gate with a lock. Another type of access control system uses an access card reader and access cards. Such access cards may be read by the access card reader by radio frequency (RF) communication or magnetically. Similar to lock and key access control systems, anybody in possession of an authorized access card can present it to the access card reader to gain access to a property. Both lock and key access control systems and access card access control systems control access to the property (or other resource) based on possession of a particular physical item, generally referred to hereinafter as token-based authentication.

Other types of access control systems control access to access-restricted resources based on possession of particular information, referred to as knowledge-based access control systems. For instance, combination/keypad locks control access by limiting access to anybody that knows a corresponding number combination, access code, password, or other information that can be entered through the combination/keypad lock. Such access control systems can also be implemented to control operational access to a computer by requiring a user to login with an authorized username and/or password, and/or to control access to online user accounts (e.g., email accounts, online banking accounts, online credit card cards, social media accounts), databases, services, information systems, or the like. In such access control systems, any user that knows the particular information can generally gain access to the computer, online user account, database, service, information system, or the like.

Still other types of access control systems control access based on what a person is, referred to as biometric access control systems. For instance, such access control systems may control access based on one or more measurable characteristics, e.g., biometric characteristics, of the person, such as fingerprints, DNA, or retinal patterns, to name a few. Biometric characteristics are distinctive, measurable characteristics of a person. In biometric-based access control systems, a person's biometric characteristics may be measured in advance and stored for later biometric authentication. When a person desires to gain access to the access-restricted resource, the person typically presents himself or herself to a biometric sensor of some sort (e.g., fingerprint scanner, retinal scanner) to newly measure the person's biometric characteristics. If the newly measured biometric characteristics match the stored biometric characteristics, the person's identity may be authenticated and the person may be granted access.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Some example embodiments described herein generally relate to wearable electronic device authentication. The authentication may be biometric based. Alternatively or additionally, the authentication may be knowledge based and/or token-based.

In an example embodiment, a method to implement multifactor authentication of a user with a wearable electronic device of the user may include performing biometric authentication of a person that bears the wearable electronic device. Performing biometric authentication may include receiving one or more first biometric signals generated by one or more sensors of the wearable electronic device, the one or more first biometric signals indicative of one or more person-specific biometric characteristics of the person; determining the one or more person-specific biometric characteristic of the person from the one or more first biometric signals; comparing the one or more person-specific biometric characteristics to one or more user-specific biometric characteristics of the user determined from one or more second biometric signals generated by the one or more sensors of the wearable electronic device at one or more previous times when the wearable electronic device was born by the user; and based on the comparing, determining a confidence level that the person is the user to determine a positive or negative authentication of the person as the user. The method may also include at least one of: performing knowledge-based authentication of the person; or presenting an access control token of the wearable electronic device to an access reader to perform token-based authentication of the person.

In another example embodiment, a non-transitory computer-readable medium having computer-executable instructions stored thereon is described. The computer-executable instructions may be executable by a processor to perform or control performance of operations to implement multifactor authentication of a user with a wearable electronic device of the user. The operations may include performing biometric authentication of a person that bears the wearable electronic device. Performing biometric authentication may include receiving one or more first biometric signals generated by one or more sensors of the wearable electronic device, the one or more first biometric signals indicative of one or more person-specific biometric characteristics of the person; determining the one or more person-specific biometric characteristic of the person from the one or more first biometric signals; comparing the one or more person-specific biometric characteristics to one or more user-specific biometric characteristics of the user determined from one or more second biometric signals generated by the one or more sensors of the wearable electronic device at one or more previous times when the wearable electronic device was born by the user; and based on the comparing, determining a confidence level that the person is the user to determine a positive or negative authentication of the person as the user. The operations may also include at least one of: performing knowledge-based authentication of the person; or presenting an access control token of the wearable electronic device to an access reader to perform token-based authentication of the person.

In another example embodiment, a wearable electronic device may include an access control token, one or more sensors, a non-transitory computer-readable medium, and a processor. The access control token may be presentable to an access reader. The one or more sensors may be configured to generate one or more first biometric signals indicative of one or more person-specific biometric characteristics of a person that bears the wearable electronic device at a first time and one or more second biometric signals indicative of one or more user-specific biometric characteristics of a user at one or more times prior to the first time and when the user associated with the wearable electronic device bears the wearable electronic device. The non-transitory computer-readable medium may be configured to store therein authentication logic. The processor may be configured to execute the authentication logic to perform or control performance of operations. The operations may include determining the one or more person-specific biometric characteristic from the one or more first biometric signals. The operations may also include determining the one or more user-specific biometric characteristic from the one or more second biometric signals. The operations may also include comparing the one or more person-specific biometric characteristics to the one or more user-specific biometric characteristics. The operations may also include, based on the comparing, determining a confidence level that the person is the user to determine a positive or negative authentication of the person as the user. The access reader may be configured to grant or deny the person access to an access-restricted resource in response to at least one of: the access control token being an authorized access control token or positive or negative authentication of the person as the user.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Figure 1:
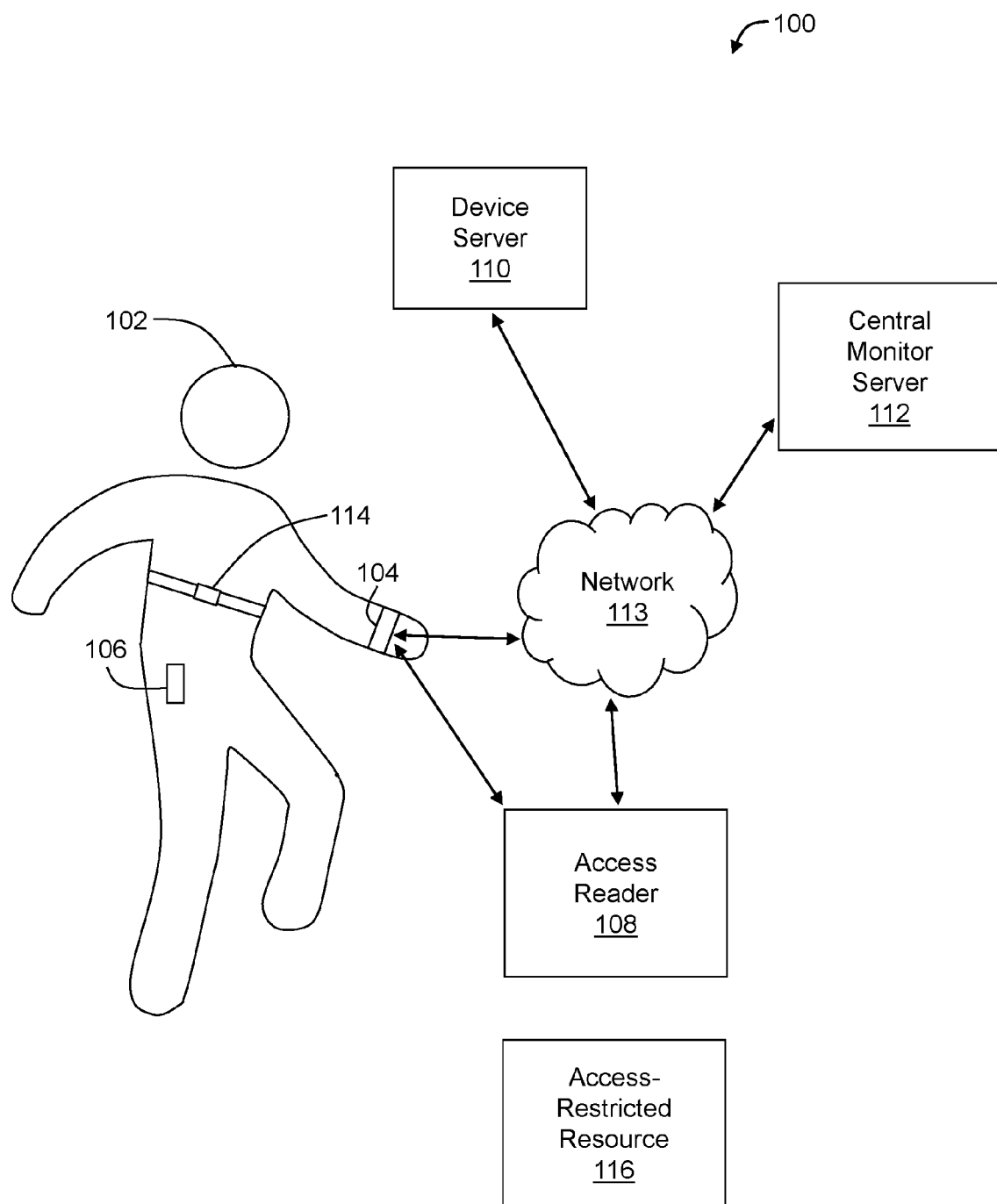
FIG. 1 illustrates an example environment in which some embodiments described herein can be implemented.

Embodiments described herein generally relate to wearable electronic device authentication based on biometric authentication as one layer or factor of authentication combined with at least one other layer or factor of authentication. In some embodiments, for instance, the biometric authentication may be supplemented with one or more challenge questions or other knowledge-based authentication, with token-based authentication, and/or with a second biometric authentication. The embodiments described herein may, e.g., simplify access control systems, reduce the cost of implementing biometric authentication in access control systems, and/or provide a variety of other improvements to access control systems.

Wearable electronic devices such as fitness trackers and other wearable electronic devices are increasing in popularity. Such wearable electronic devices add to an increasing number of items that a person may carry around on a regular basis and must keep track of, including access cards that may provide access to a residence (house or apartment), common areas (e.g., community pool, clubhouse), work place, as well as potentially other access cards. According to some embodiments described herein, hardware and/or information included in and used to authenticate such access cards may be included in a wearable electronic device, eliminating the need for a separate access card. The hardware and/or information included in and used to authenticate such access cards may be referred to as an access control token. The access control token included in the wearable electronic device may be presented to and read by an access reader that controls access to an access-restricted resource to gain access to the access-restricted resource. The access-restricted resource may include information (e.g., an email account, online account, information database), a vehicle, a device (e.g., a computer), a system (e.g., an IT system), a physical location (e.g., residence, work place, community common area), or other access-restricted resource.

Alternatively or additionally, the wearable electronic device may be used to implement authentication of the person bearing the wearable electronic device. The authentication of the person may include biometric authentication and/or knowledge-based authentication of the person. In these and other embodiments, the wearable electronic device may generally include one or more sensors to measure biometric characteristics of the person, e.g., in real time or substantially in real-time. Newly measured biometric characteristics may be compared against previously measured and stored biometric characteristics to authenticate (or not) the person bearing the wearable electronic device as a particular user associated with the wearable electronic device.

In some cases, a negative biometric authentication of the person may be made (e.g., the person may not be authenticated biometrically as being the particular user) even if the person really is the particular user. This scenario is being referred to as a false negative and may occur for any of a variety of reasons. In response to a negative biometric authentication, the wearable electronic device may present a challenge question to the person or otherwise request certain knowledge (e.g., password, personal identification number (PIN)) assumed to be known by the particular user from the person. If the person's answer is correct (or if the person has the knowledge assumed to be known by the particular user), a positive authentication of the person as the particular user may be made (e.g., the person may be authenticated as being the particular user) notwithstanding the negative biometric authentication. If the person's answer is incorrect or the person does not answer the challenge question, a negative authentication may be made.

Alternatively or additionally, in some cases where a positive biometric authentication of the person is made, the wearable electronic device may nevertheless present a challenge question to the person or otherwise request certain knowledge assumed to be known by the particular user from the person. The wearable electronic device may present one or more challenge questions to the person after a positive biometric authentication of the person is made with some random or pseudorandom probability or in response to an external indication (e.g., from a server). As described above, if the person's answer is correct a positive authentication of the person as the particular user may be made, or if the person's answer is incorrect a negative authentication of the person as the particular user may be made.

In examples that include the access reader, the access reader's grant or denial of access to the access-restricted resource may depend on at least whether the access control token included in the wearable electronic device indicates that the wearable electronic device is authorized to access the access-restricted resource. The access reader's grant or denial of access may additionally depend on the positive or negative authentication of the person by the wearable electronic device. For example, the access reader may grant the person access only if both the access information indicates the wearable electronic device is authorized and the wearable electronic device makes a positive authentication of the person.

In other embodiments, the access reader may grant the person access if the access control token indicates the wearable electronic device is authorized, whether or not a positive authentication of the person is made. In these and other embodiments, a followup may be triggered in response to negative authentication of the person that would not be triggered in response to positive authentication of the person. For example, the negative authentication may be reported to the access reader or a server (e.g., a central monitor server or a device server as described below). The access reader or the server may then send a notification regarding the negative authentication to a communication address (e.g., email address, mobile device number) associated with the particular user. Alternatively or additionally, the access reader or the server may notify human security (e.g. a security guard) to authenticate the person face to face or visually through a surveillance system. The followup that is triggered can include any other action desired for the access control system.

The access reader may be operably coupled to, e.g., a lock on a door or gate to the access-restricted resource in an embodiment in which the access-restricted resource is a physical location. In some embodiments, the access reader may grant the person access to the access-restricted resource by, e.g., controlling the lock to unlock to allow the person to pass through the door or gate to the access-restricted resource. Alternatively or additionally, the access reader may be communicably coupled to a software program or other code that may grant the person access to the access-restricted resource, e.g., by logging the person in to a computer, an online user account, a database, a service, or an information system.

Reference will now be made to the drawings to describe various aspects of some example embodiments of the disclosure. The drawings are diagrammatic and schematic representations of such example embodiments, and are not limiting of the present disclosure, nor are they necessarily drawn to scale.

FIG. 1 illustrates an example environment 100 in which some embodiments described herein can be implemented. The environment 100 includes a person 102, a wearable electronic device 104, a smartphone 106, and an access reader 108. The environment 100 may additionally include a device server 110, a central monitor server 112, and/or a network 113.

The network 113 may include one or more wide area networks (WANs) and/or local area networks (LANs) that enable the wearable electronic device 104, the access reader 108, the device server 110, and/or the central monitor server 112 to communicate with each other. In some embodiments, the network 113 includes the Internet, including a global internetwork formed by logical and physical connections between multiple WANs and/or LANs. Alternately or additionally, the network 113 may include one or more cellular RF networks and/or one or more wired and/or wireless networks such as, but not limited to, 802.xx networks, Bluetooth access points, wireless access points, IP-based networks, or the like. The network 113 may also include servers that enable one type of network to interface with another type of network.

The environment 100 additionally includes one or more sensors. Each of the sensors is configured to generate signals indicative of physical activities performed by the person 102 and/or of biometric characteristics of the person 102. A signal generated by a sensor may in some examples below be referred to as a biometric signal when it is indicative of one or more biometric characteristics of the person 102. The wearable electronic device 104 and/or the device server 110 may be configured to determine or extract one or more biometric characteristics of the person 102 from the signals generated by the sensors.

All of the sensors may be included in a single device, such as the wearable electronic device 104 or the smartphone 106. Alternately or additionally, the sensors may be distributed between two or more devices. For instance, one or both of the wearable electronic device 104 or the smartphone 106 may include a sensor. Alternately or additionally, the one or more sensors may be provided as separate sensors that are separate from either of the wearable electronic device 104 or the smartphone 106 and are configured to be carried by the person 102. For instance, a sensor 114 is provided as a separate sensor. In particular, the sensor 114 is separate from the wearable electronic device 104 and the smartphone 106, and is embodied in FIG. 1 as a chest-strap style heart rate monitor or other physiological sensor configured to be worn by the person 102.

In some embodiments, the sensor 114 can include a sensor attached to or otherwise born on the body of the person 102. Various non-limiting examples of sensors that may be attached to the body of the person 102 and that may be implemented as the sensor 114 and/or as the sensor(s) included in the wearable electronic device 104 or the smartphone 106 include heart rate sensors (e.g., pulse oximeters), electrocardiography (ECG) sensors, breathing sensors, blood pressure sensors, gait sensors (e.g., accelerometers, step-counters), or other suitable sensors.

As already mentioned, the sensors may each be configured to generate signals indicative of physical activities performed by the person 102 and/or of biometric characteristics of the person 102. For instance, in the illustrated embodiment, the person 102 is walking, and each sensor may collect a signal indicative of the person 102 walking and/or of the gait of the person 102, the heart rate of the person 102, and/or other biometric characteristics of the person. Of course, the person 102 may perform any of a variety of physical activities including, but not limited to, ascending stairs, descending stairs, walking, running, hiking, road biking, mountain biking, roller blading, roller skating, hang gliding, or performing some other physical activity.

Where the sensors include a gait sensor, the biometric characteristics determined from the signals generated by the sensors may include, e.g., gait cadence, step length, timing or other characteristics of stance phase, push-off phase, swing phase, and/or heel-strike phase, and/or a classification of the gait based on one or more of the foregoing. Alternatively or additionally, the biometric characteristics and/or the determination thereof in the case of an accelerometer used as a gait sensor may be implemented as described in U.S. Patent Publication No. 2015/0112603, which is incorporated herein by reference in its entirety.

Where the sensor includes a heart rate sensor, the biometric characteristics determined from the signals generated by the sensors may include, e.g., heart rate, photoplethysmograph (PPG) shape, and/or PPG harmonics. Heart rate, PPG shape, PPG harmonics and/or some other biometric characteristics individually may be insufficient to uniquely identify or authenticate the person 102. In these and other embodiments, such biometric characteristics may be combined with other biometric characteristics which together may be sufficient to uniquely identify or authenticate the person 102. For instance, heart rate and PPG shape together may be sufficient to uniquely identify or authenticate the person 102, as described in U.S. Patent Publication No. 2015/0109124, which is incorporated herein by reference.

Alternatively or additionally, the sensor or sensors may include one or more of an ECG sensor, an electrodermal activity (EDA) or galvanic skin response sensor, or other suitable sensor to generate ECG and/or EDA signals from which ECG and/or EDA biometric characteristics may be determined. Alternatively or additionally, the biometric characteristics may include one or more of electrical skin impedance, respiratory rate, heart rate, heart rate variability, PPG morphology, or vocal sound frequency.

The wearable electronic device 104 may be embodied as a portable electronic device and may be born by the person 102 throughout the day and/or at other times. The wearable electronic device 104 may be worn on a wrist of the person 102 as illustrated in FIG. 1, may be carried in a pocket or clipped to a belt of the person 102, or may be born in some other manner by the person 102. As used herein, "born by" means carried by and/or attached to. The wearable electronic device 104 may be configured to, among other things, analyze signals collected by one or more sensors within the environment 100 to determine biometric characteristics of the person 102. In these and other embodiments, the wearable electronic device 104 may be a device dedicated for performing such functionality. The wearable electronic device 104 may include at least one onboard sensor for collecting such signals. Alternately or additionally, the smartphone 106 may include at least one sensor and may communicate signals collected by its onboard sensor to the wearable electronic device 104, and/or the wearable electronic device 104 may communicate with the sensor 114 or other separate sensors to receive signals collected by the sensor 114 or other separate sensor(s).

Alternately or additionally, the device server 110 may be configured to receive signals collected by one or more sensors or other devices, such as the wearable electronic device 104 or smartphone 106, within the environment 100. The device server 110 may be further configured to analyze the received signals to determine biometric characteristics of the person 102 and/or identify one or more activities performed by the person 102. The signals may be collected by one or more sensors in the wearable electronic device 104, one or more sensors in the smartphone 106, and/or the sensor 114 or other separate sensor(s).

The wearable electronic device 104 may include an access control token that may be read by the access reader 108. The access reader 108 controls access to an access restricted resource 116. The access reader 108 may grant or deny the person 102 access to the access-restricted resource 116 depending on at least whether the wearable electronic device 104 includes the access control token that indicates the wearable electronic device 104 is authorized to access the access-restricted resource 116. More generally, the access reader 108 may grant or deny access to the access-restricted resource depending on whether the person 102 passes a multifactor authentication that includes biometric authentication combined with at least one of token-based authentication or knowledge-based authentication.

In these and other embodiments, the wearable electronic device 104 may perform authentication of the person 102 to determine whether the person 102 is a particular user associated with the wearable electronic device 104. The authentication may include at least biometric authentication, which may include biometric gait authentication as described in U.S. Patent Publication No. 2015/0112603. Alternatively or additionally, the biometric authentication may include authentication based on both heart rate and photoplethysmograph (PPG) shape, as described in U.S. Publication No. 2015/0109124. Alternatively or additionally, the biometric authentication may include authentication based on one or more other biometric characteristics, examples of which are listed elsewhere herein.

The authentication performed by the wearable electronic device 104 may in some embodiments additionally include knowledge-based authentication. In these and other embodiments, the particular user may own the wearable electronic device 104, may use it exclusively or substantially exclusively, or may otherwise be associated with the wearable electronic device 104. Accordingly, the wearable electronic device 104 may receive signals indicative of biometric characteristics of the particular user from the sensors while the wearable electronic device 104 is in use by the particular user. The wearable electronic device 104 and/or the device server 110 may determine the biometric characteristics of the particular user (e.g., from the signals) and store them for future reference, e.g., as a biometric signature. The wearable electronic device 104 and/or the device server 110 may subsequently perform the authentication by receiving one or more signals indicative of the biometric characteristics of the person 102 generated by the sensors as the person 102 is at or approaching or near the access reader 108. The wearable electronic device 104 and/or the device server 110 may determine the biometric characteristics of the person from the signals and compare them to the biometric characteristics previously determined (e.g., the biometric signature) for the particular user associated with the wearable electronic device 104 to determine a confidence level that the person 102 is the particular user.

If the confidence level is above a threshold confidence level, a positive authentication of the person 102 as the particular user may be made, indicating that the person 102 is the particular user. If the confidence level is below the threshold confidence level, a negative authentication of the person 102 as the particular user may be made, indicating that the person 102 is not the particular user.

In some embodiments, a challenge question may be presented to the person 102 through the wearable electronic device 102, through the smartphone 106, or through some other device. The challenge question may be presented to the person 102 with some random or pseudorandom probability or in response to an external indication (e.g., from the device server 110 or central monitor server 112) even if the confidence level is above the threshold confidence level, e.g., after a positive biometric authentication of the person 102. Alternatively or additionally, the challenge question may be presented to the person 102 in response to the confidence level being below the threshold confidence level. In these and other embodiments, the positive authentication of the person 102 as the particular user may be made if the person 102 provides an answer to the challenge question through the wearable electronic device 104, the smartphone 106, or other device that matches an expected answer to the challenge question even if the confidence level based on the biometric authentication is below the threshold confidence level. On the other hand, if the person 102 does not answer the challenge question at all or if the person 102 provides an answer to the challenge question that does not match the expected answer, the negative authentication may be made. Presenting a challenge question to the person 102 should be broadly construed to include requesting information from the person 102, which information is presumed to be known by the particular user, such as a password, PIN, or other information.

The positive or negative authentication may be reported to the access reader 108 and/or to the central monitor server 112. In some embodiments, the access reader 108 may grant the person 102 access to the access-restricted resource 116 only if both the wearable electronic device 104 includes the access control token that indicates the wearable electronic device 104 is authorized to access the access-restricted resource 116 as determined by the access reader 108 and if a positive authentication is made by the wearable electronic device 104 or device server 110 and reported to the access reader 108. More generally, the access reader 108 may grant the person 102 access to the access-restricted resource 116 if the person 102 passes a multifactor authentication that includes both biometric authentication and at least one of token-based authentication or knowledge-based authentication.

In other embodiments, the access reader 108 may grant the person 102 access to the access-restricted resource 116 if the wearable electronic device 104 includes the access control token that indicates the wearable electronic device 104 is authorized to access the access-restricted resource 116 as determined by the access reader 108, even if a negative authentication is made by the wearable electronic device 104 or device server 110 and reported to the access reader 108. In these and other embodiments, the negative authentication may trigger a followup of some sort. The followup may be triggered by reporting the negative authentication to the access reader 108, the central monitor server 112, and/or the device server 110 or otherwise causing the followup to occur.

The followup may include sending a notification regarding the negative authentication to a communication address associated with the particular user. The communication address may include an email address, a mobile phone number, or other communication address. The notification may serve to notify the particular user that the person 102 currently bearing the wearable electronic device 104 failed the biometric authentication and/or the knowledge-based authentication. If the negative authentication is a false negative and the person 102 really is the particular user, the particular user can disregard the notification. On the other hand, if the negative authentication is not a false negative, the notification may serve to notify the particular user that a person (e.g., the person 102) that is not the particular user is in possession of the wearable electronic device 104 and/or that the person 102 has gained access to the access-restricted resource 116 despite not being the particular user.

As another example, the central monitor server 112 may be part of a security system or access control system with one or more access readers, a surveillance system, and/or human security (e.g., security guards). In these and other embodiments, the followup may include notifying the human security to authenticate the person face to face or through the surveillance system. If the human security determines (based on viewing the person face to face or through the surveillance system) that the person is the particular user, nothing further need be done. If, however, the human security determines that the person is not the particular user, the person may be questioned, removed from the premises (e.g., from the access-restricted resource), or some other action may be taken. In other embodiments, the followup triggered in response to the negative authentication may include one or more other actions.

Figure 2:
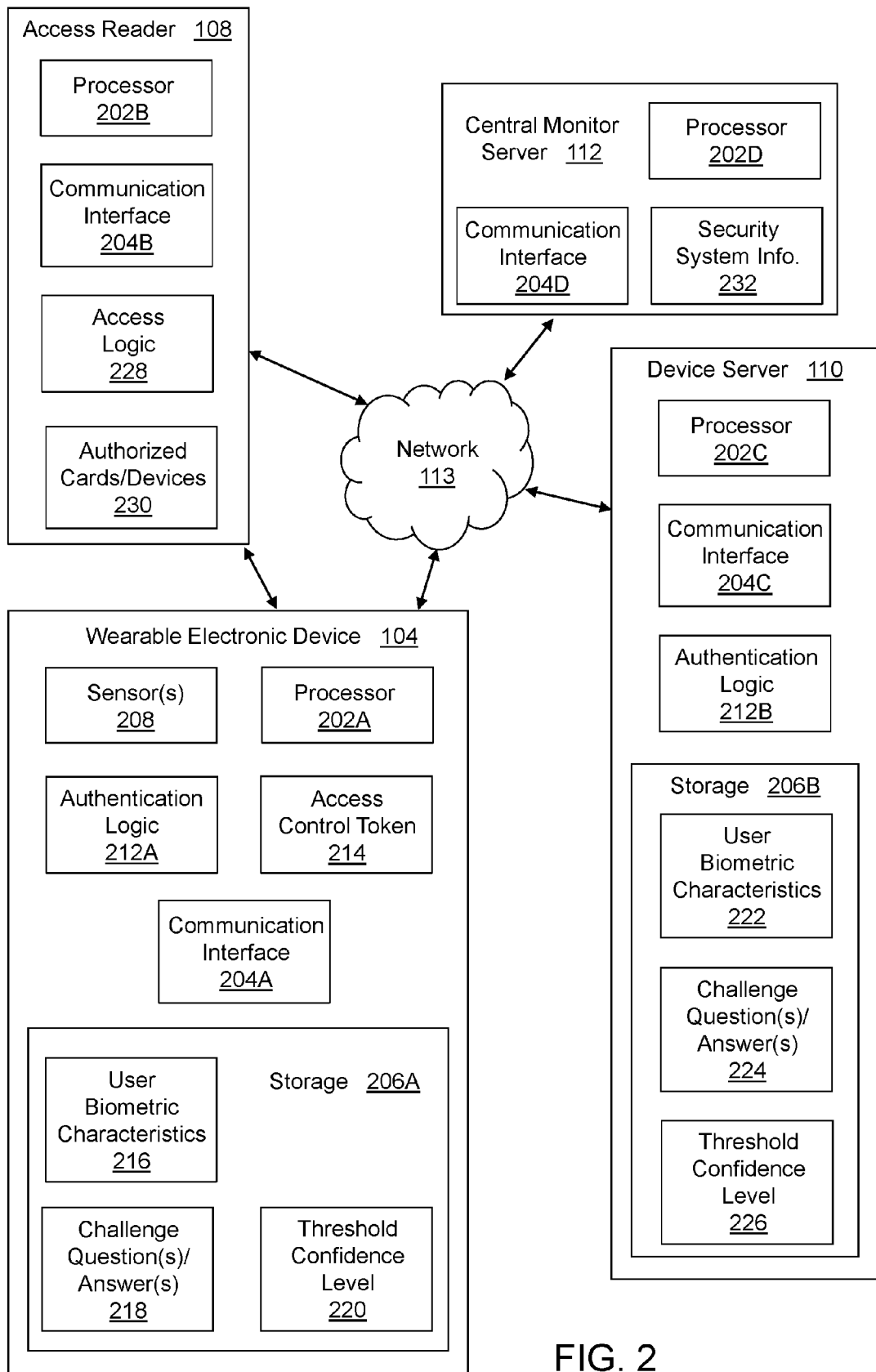
FIG. 2 is a block diagram of a wearable electronic device, an access reader, a device server, and a central monitor server of FIG. 1.

FIG. 2 is a block diagram of the wearable electronic device 104, the access reader 108, the device server 110, and the central monitor server 112 of FIG. 1, arranged in accordance with at least one embodiment described herein. Each of the wearable electronic device 104, the access reader 108, the device server 110, and the central monitor server 112 may include a processor 202A, 202B, 202C, or 202D (generically "processor 202" or "processors 202"), a communication interface 204A, 204B, 204C, or 204D (generically "communication interface 204" or "communication interfaces 204"), and a storage and/or memory 206A, 206B (generically "storage 206").

Each of the processors 202 may include an arithmetic logic unit, a microprocessor, a general-purpose controller, or some other processor or array of processors, to perform or control performance of operations as described herein. The processors 202 may be configured to process data signals and may include various computing architectures including a complex instruction set computer (CISC) architecture, a reduced instruction set computer (RISC) architecture, or an architecture implementing a combination of instruction sets. Although each of the wearable electronic device 104, the access reader 108, the device server 110, and the central monitor server 112 of FIG. 2 includes a single processor 202, multiple processor devices may be included and other processors and physical configurations may be possible. The processor 202 may be configured to process any suitable number format including, but not limited to two's compliment numbers, integers, fixed binary point numbers, and/or floating point numbers, all of which may be signed or unsigned.

Each of the communication interfaces 204 may be configured to transmit and receive data to and from other devices and/or servers through a network bus, such as an I²C serial computer bus, a universal asynchronous receiver/transmitter (UART) based bus, or any other suitable bus. In some implementations, each of the communication interfaces 204 may include a wireless transceiver for exchanging data with other devices or other communication channels using one or more wireless communication methods, including IEEE 802.11, IEEE 802.16, BLUETOOTH®, Wi-Fi, Zigbee, near field communication (NFC), or another suitable wireless communication method.

In FIG. 2, only the wearable electronic device 104 and the device server 110 are illustrated as including storage 206. The access reader 108 and the central monitor server 112 may also include storage, though not illustrated in FIG. 2. The storage 206 may include a non-transitory storage medium that stores instructions or data that may be executed or operated on by a corresponding one of the processors 202. The instructions or data may include programming code that may be executed by corresponding one of the processors 202 to perform or control performance of the operations described herein. The storage 206 may include a non-volatile memory or similar permanent storage media including a flash memory device, an electrically erasable and programmable read only memory (EEPROM), a magnetic memory device, an optical memory device, or some other mass storage for storing information on a more permanent basis. In some embodiments, the storage 206 may also include volatile memory, such as a dynamic random access memory (DRAM) device, a static random access memory (SRAM) device, or the like.

The wearable electronic device 104 may additionally include one or more sensors 208, authentication logic 212A, and/or an access control token 214. The storage 206A of the wearable electronic device 104 may include one or more user biometric characteristics 216 (or a user biometric signature), one or more challenge questions and/or corresponding answers 218 (hereinafter "challenge question(s)/answer(s) 218") or other information assumed to be known to the particular user associated with the wearable electronic device 104, and/or a threshold confidence level 220.

The sensor 208 may represent any hardware or software sensor capable to detect biometric characteristics of the particular user and/or the person 102 of FIG. 1. As already suggested above, the sensor 208 may include a heart rate sensor, a breathing sensor, a blood pressure sensor, or a gait sensor. Alternatively or additionally, the sensor 208 may include a gyroscope, an altimeter, a global positioning system (GPS) sensor, a pedometer, a magnetometer, a thermometer, a humidity sensor, a barometric pressure sensor, any other sensor that may detect motion, environmental, or human state, or any combination thereof. While only a single sensor 208 is illustrated in FIG. 2, more generally the wearable electronic device 104 may include one or more sensors.

The authentication logic 212A may include code such as computer-readable instructions that may be executable by the processor 202A of the wearable electronic device 104 to perform or control performance of one or more authentication methods or operations as described herein. An example authentication method that may be performed or controlled by execution of the authentication logic 212A is described below with respect to FIG. 4 and may be biometric based, knowledge based, or both. The authentication logic 212A may be stored in the storage 206A or other non-transitory medium.

The access control token 214 may include hardware and/or information included in and used to authenticate the wearable electronic device 104 as authorized to access the access restricted resource 116 of FIG. 2. For example, the access control token 214 may include a RF identification (RFID) tag or transponder, in which case the access reader 108 may include a RFID transceiver to read the RFID tag or transponder. For instance, the communication interface 204B of the access reader 108 may include the RFID transceiver. In these and other embodiments, the access reader 108 and the access control token 214 and/or the wearable electronic device 104 may communicate with each other and/or implement access control methods as described in U.S. Pat. No. 7,775,429, which is incorporated herein by reference. Alternatively or additionally, the access control token 214 may include an optically transmissive material having gradient refractive index and diffusive properties which provide the material with a non-duplicatable quality, with optical information encoded thereon, as described in U.S. Pat. No. 5,283,431, which is incorporated herein by reference. Alternatively or additionally, the access control token 214 may include a smart card or other security token or other suitable access control token.

The user biometric characteristics 216 may alternatively be referred to as a biometric signature of the particular user associated with the wearable electronic device 104. The user biometric characteristics 216 may include one or more biometric characteristics of the particular user determined by the processor 202 from one or more signals received from and generated by the sensor 208 when the wearable electronic device 104 is born by the particular user.

The challenge question(s)/answer(s) 218 may include one or more challenge questions and corresponding answers to the one or more challenge questions of the particular user associated with the wearable electronic device 104. When the challenge question(s)/answer(s) 218 are initially created and stored in storage 206A, the particular user may select the one or more challenge questions from a list of challenge questions and/or may generate the one or more challenge questions manually. The particular user may also enter answers to the challenge questions. The challenge questions may be selected and/or the answers may be entered through the wearable electronic device 104. Alternatively or additionally, the challenge questions may be selected and/or the answers may be entered online, e.g., during a registration of the wearable electronic device 104. The answers entered by the particular user to the challenge questions, e.g., during registration of the wearable electronic device 104, may be referred to as expected answers during the authentication methods described herein.

The threshold confidence level 220 may be used as a point of comparison for making a positive or negative authentication of the person 102 as the particular user. For instance, in some embodiments, when a confidence level determined from biometric authentication that the person 102 is the particular user exceeds the threshold confidence level 220, a positive authentication that the person 102 is the particular user may be made. When the confidence level determined from biometric authentication that the person 102 is the particular user is less than the threshold confidence level 220, a negative authentication of the person 102 as the particular user may be made.

Analogous to the authentication logic 212A, the authentication logic 212B may include code such as computer-readable instructions that may be executable by the processor 202C of the device server 110 to perform or control performance of one or more authentication methods or operations as described herein. An example authentication method that may be performed or controlled by execution of the authentication logic 212B is described below with respect to FIG. 4 and may be biometric based, knowledge based, or both. The authentication logic 212B may be stored in the storage 206B or other non-transitory medium.

Analogous to the user biometric characteristics 216, the user biometric characteristics 222 may alternatively be referred to as biometric signatures of multiple particular users associated with different wearable electronic devices that may include the wearable electronic device 104. The user biometric characteristics 216 may include one or more biometric characteristics of the particular users determined by the processors of those wearable electronic devices and/or determined by the processor 202C of the device server 110. In some embodiments, signals generated by sensors of the wearable electronic devices (such as by the sensor 208) when the wearable electronic devices are born by the particular users may be transmitted by the wearable electronic devices to the device server 110. The processor 202C of the device server 110 may determine the user biometric characteristics 222 of the particular users from the signals received from the wearable electronic devices.

Analogous to the challenge question(s)/answer(s) 218, the challenge question(s)/answer(s) 224 may include one or more challenge questions and corresponding answers to the one or more challenge questions of the particular users associated with the wearable electronic devices. The particular users may individually select the one or more challenge questions from a list of challenge questions and/or may generate the one or more challenge questions manually. The particular users may also enter answers to the challenge questions. The challenge questions may be selected and/or the answers may be entered through the wearable electronic devices. Alternatively or additionally, the challenge questions may be selected and/or the answers may be entered online, e.g., during a registration of the wearable electronic devices. The answers entered by the particular users to the challenge questions, e.g., during registration of the wearable electronic devices, may be referred to as expected answers during the authentication methods described herein.

Analogous to the threshold confidence level 220, the threshold confidence level 226 may be used as a point of comparison for making a positive or negative authentication of persons bearing the wearable electronic devices as the particular users. For instance, in some embodiments, when a confidence level determined from biometric authentication that a person is a corresponding particular user exceeds the threshold confidence level 226, a positive authentication that the person is the particular user may be made. When the confidence level determined from biometric authentication that the person is the particular user is less than the threshold confidence level 226, a negative authentication of the person as the particular user may be made.

Because the device server 110 includes user biometric characteristics 222 and challenge question(s)/answer(s) 224 of multiple users, the device server 110 may be used to authenticate multiple bearers of the various wearable electronic devices, as opposed to authentication of a single person bearing a single wearable electronic device.

Alternatively or additionally, the device server 110 may match wearable electronic devices against identities of the particular users and/or take one or more actions in the event of a non-match. In these and other embodiments, each incoming sensor signal from a wearable electronic device may include an identifier of the wearable electronic device and the device server 110 may include a list, table, or other data structure that indicates which wearable electronic devices are associated with which particular users. The authentication logic 212B may authenticate the person bearing the wearable electronic device as one of the particular users for which the device server 110 includes user biometric characteristics 222. The device server 110 may also check the identifier of the wearable electronic device against the list, table, or other data structure to determine whether the particular user as which the person has been authenticated is the same particular user associated with the wearable electronic device. If not, the device server 110 may send a notification to a communication address of the particular user with which the wearable electronic device is associated to notify the particular user that the particular user's wearable electronic device is being born by a person not authenticated as the particular user.

For instance, a wearable electronic device A may be associated with a particular user A and a wearable electronic device B may be associated with a particular user B. If a positive authentication is made by the device server 110 that a person bearing the wearable electronic device A is the particular user B (e.g., a non-match between the authenticated particular user B and the associated particular user A of the wearable electronic device A), the device server 110 may notify the particular user A (e.g., by sending a notification to a communication address of the particular user A) that the wearable electronic device A is being born by a person other than the particular user A, or that the wearable electronic device A is being born specifically by a person authenticated as the particular user B. Alternatively or additionally, the device server 110 may take some other action instead of or in addition to notifying the particular user A.

The access reader 108 may include access logic 228 and a list, table, or other data structure of ID numbers or other identifying information of authorized cards/devices 230 (hereinafter "authorized cards/devices 230"). As previously mentioned, in the event the access control token 214 of the wearable electronic device 104 includes a RFID tag or transponder, the access reader 108 may include a RFID transceiver to read the RFID tag or transponder. For instance, the communication interface 204B may include or be implemented as a RFID transceiver. Alternatively or additionally, where the access control token 214 of the wearable electronic device 104 includes an optically transmissive material having gradient refractive index and diffusive properties which provide the material with a non-duplicatable quality, with optical information encoded thereon, the communication interface 204B of the access reader 108 may include one or more laser diodes or other optical emitters and one or more photodiodes, charge coupled devices (CCDs), or other optical receivers to read the access control token 214 of the wearable electronic device 104. Alternatively or additionally, the communication interface 204B may include other suitable hardware and/or software to read other types of access control tokens 214.

In the example of the access control token 214 including a RFID tag or transponder and the communication interface 204B including a RFID transceiver, the access control token 214 may be read as follows. The RFID transceiver of the access reader 108 may transmit a RF query to the RFID tag or transponder of the access control token 214 as the access control token 214 passes over or near (e.g., within a predetermined proximity) of the RFID transceiver. The RFID tag or transponder of the access control token 214 may include a silicon chip and an antenna that enables the RFID tag or transponder to receive and respond to the RF query. The response may typically include a RF signal that includes a pre-programmed identification (ID) number. The access reader 108 (or more particularly, the RFID transceiver) may receive the signal and the access logic 228 of the access reader 108 may compare the pre-programmed ID number from the RF signal to the list of authorized cards/devices 230.

If the pre-programmed ID number from the RF signal is in the list of authorized cards/devices 230 or the access logic 228 otherwise determines that the access control token 214 is an authorized access control token 214, the access logic 228 may grant the person bearing the wearable electronic device 104 access to the access-restricted resource 116. Otherwise, the person may be denied access. Alternatively or additionally, the person may be granted access only if it is determined by the access logic 228 that both the access control token 214 is an authorized access control token and a positive authentication has been made that the person is the particular user associated with the wearable electronic device 104. Accordingly, the access logic 228 in at least some embodiments may receive authentication information reported by the wearable electronic device 104 indicating whether the person bearing the wearable electronic device 104 has received a positive authentication or a negative authentication.

The central monitor server 112 may include security system information 232. The security system information 232 may include reported authentication information from the wearable electronic device 104 for every read of the access control token 214 by the access reader 108. Alternatively, the security system information 232 may include reported authentication information that is reported only in the event of a negative authentication. Alternatively or additionally, the security system information 232 may identify surveillance cameras and/or human security at or near the access reader 108 that can be used to follow up in embodiments where a person that receives a negative authentication is granted access to the access-restricted resource by virtue of having an authorized access control token 214.

Figure 3A:
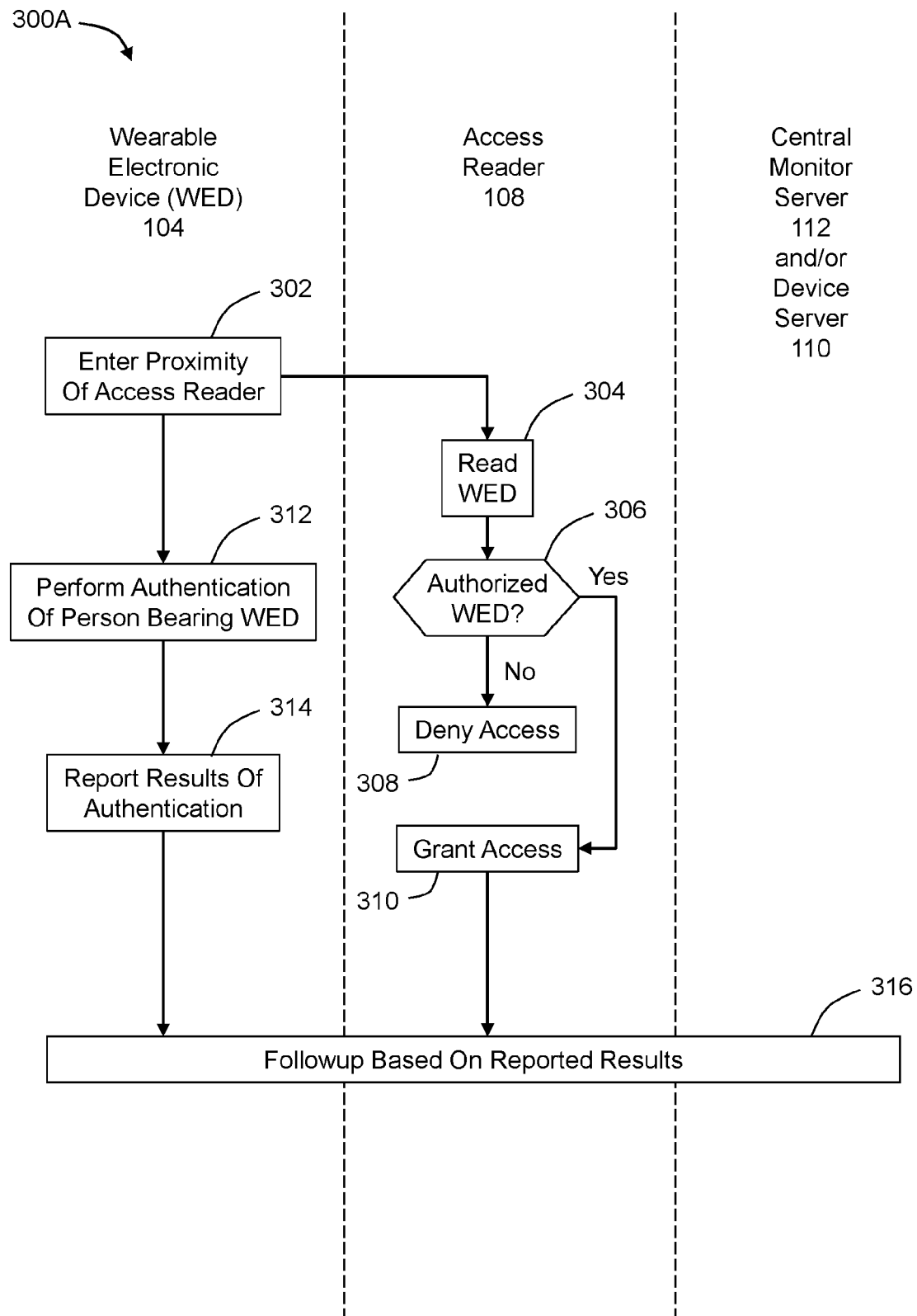
FIGS. 3A-3C include flow charts of three example access control methods.
Figure 3B:
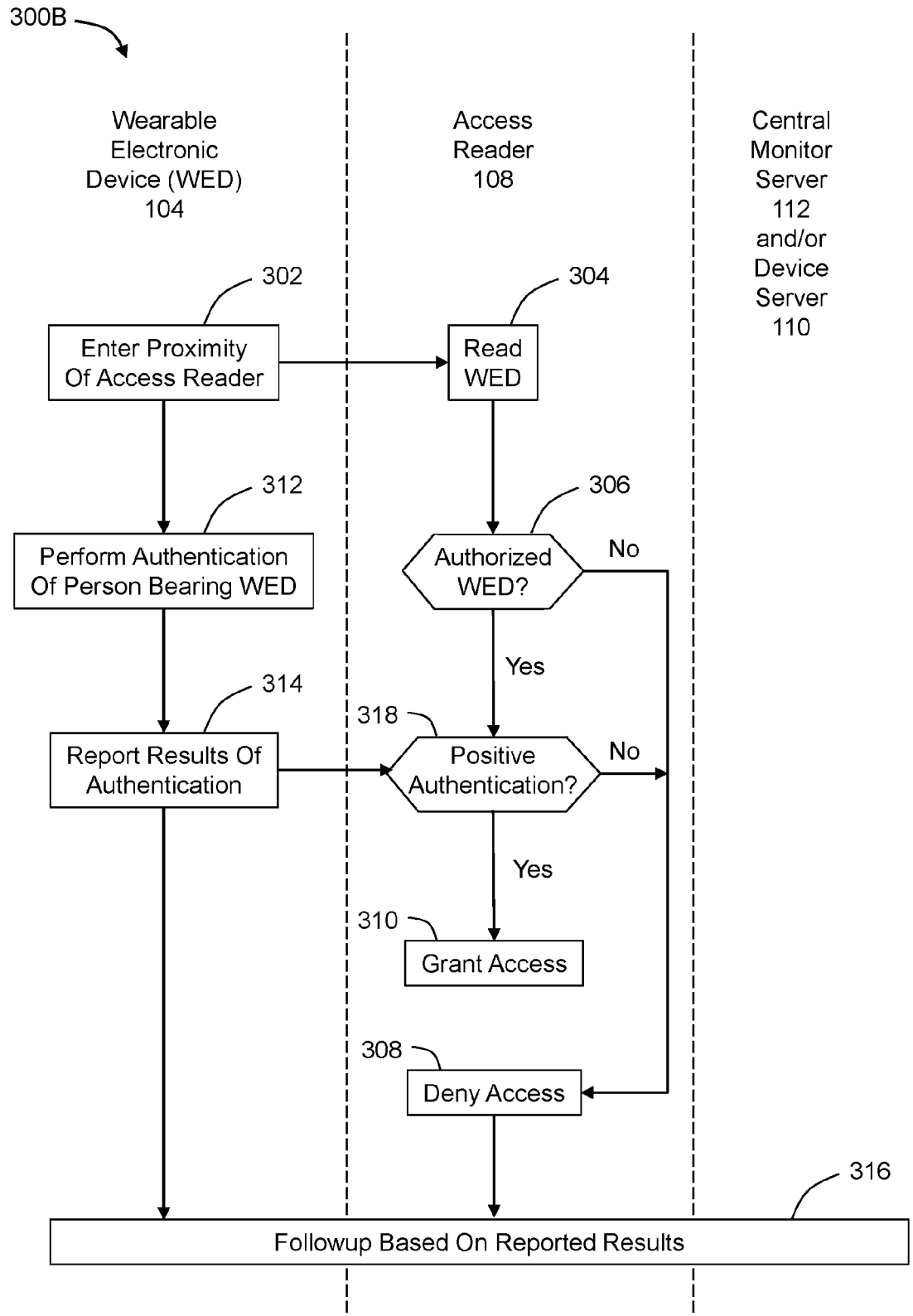
Figure 3C:
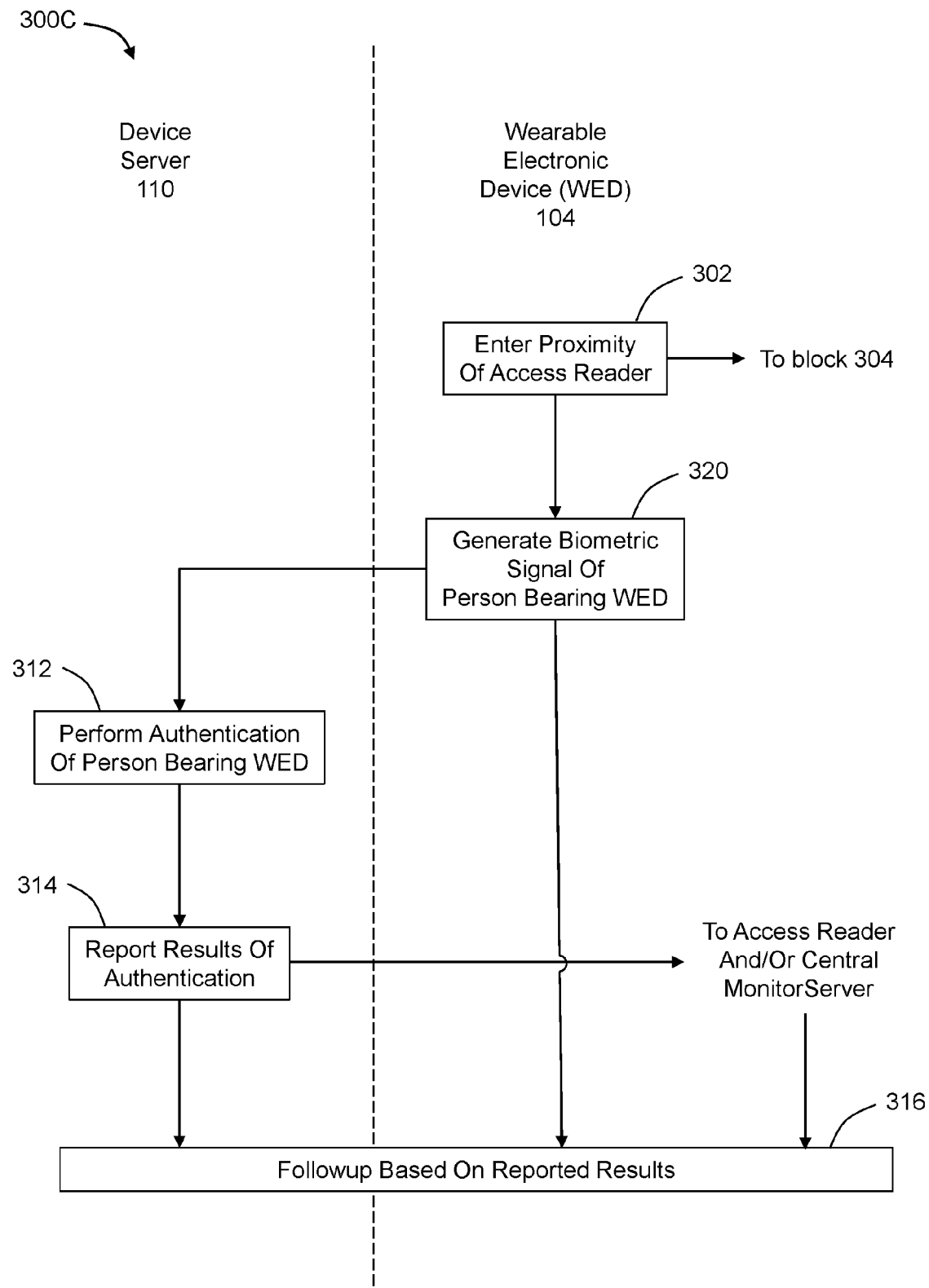

FIGS. 3A-3C include flow charts of three example access control methods 300A, 300B, 300C (generically "methods 300"), each arranged in accordance with at least one embodiment described herein. Each of FIGS. 3A-3C is divided into three columns (FIGS. 3A and 3B) or two columns (FIG. 3C) with a column header indicating an entity (e.g., wearable electronic device 104, access reader 108, device server 110, or central monitor server 112) that perform or control performance of operations within the corresponding column according to some embodiments. According to the method 300A of FIG. 3A, access to the access-restricted resource 116 depends on whether the wearable electronic device 104 includes an authorized access control token where authentication of the person 102 by the wearable electronic device 104 is used as input in any followup that may occur without being used to determine whether to grant or deny access. According to the method 300B of FIG. 3B, access to the access-restricted resource 116 depends on both whether the wearable electronic device 104 includes an authorized access control token and whether a positive authentication of the person 102 as the particular user is made. In the methods 300A and 300B of FIGS. 3A and 3B, authentication is performed by the wearable electronic device 104. According to the method 300C of FIG. 3C, authentication is instead performed by the device server 110.

Each of the methods 300A-300C will be discussed in turn, beginning with the method 300A of FIG. 3A.

The method 300A of FIG. 3A may begin at block 302, in which the wearable electronic device 104 born by the person 102 enters a proximity of the access reader 108. Throughout the blocks of FIGS. 3A-3C and in some other figures, the term "wearable electronic device" is abbreviated as "WED." Block 302 may be followed by block 304 and block 312. The wearable electronic device 104 entering the proximity of the access reader 108 may include the wearable electronic device 104 coming within a predetermined distance of the access reader 108 and/or coming close enough to the access reader 108 to receive a query from the access reader 108.

At block 304, the access reader 108 may read the wearable electronic device 104. More particularly, the access reader 108 may read the access control token 214 of the wearable electronic device 104.

At block 306, the access reader 108 may determine whether the wearable electronic device 104 is an authorized wearable electronic device. For instance, the access reader 108 may determine whether a pre-programmed ID read from the access control token 214 by the access reader 108 is in the list of authorized cards/devices 230 to determine whether the wearable electronic device 104 is an authorized electronic device. If not, the method 300A may proceed to block 308 where access to the access-restricted resource 116 may be denied to the person 102 bearing the wearable electronic device 102. If so, the method 300A may proceed to block 310 where access to the access-restricted resource 116 may be granted to the person 102 bearing the wearable electronic device 102.

At block 312, the wearable electronic device 104 may perform authentication of the person 102 bearing the wearable electronic device to make a positive or negative authentication of the person 102 as the particular user associated with the wearable electronic device 104. The wearable electronic device 104 may perform the authentication in response to determining that the wearable electronic device 104 is within proximity of the access reader 108, e.g., within a threshold distance from the access reader 108 such as within a few feet or a few yards of the access reader 108. The wearable electronic device 104 may determine that it is within proximity of the access reader 108 in response to detecting a beep or chirp (e.g., using an appropriate sensor) that may be emitted by the access reader 108 when it reads the wearable electronic device 104 at block 304 or in response to receiving a query (e.g., using the access control token 214 and/or the communication interface 204A) from the access reader 108 when it reads the wearable electronic device 104 at block 304. Alternatively or additionally, the wearable electronic device 104 may detect its location (e.g., using an appropriate sensor such as GPS) as being within the proximity of a known location of the access reader 108. In other embodiments, the wearable electronic device 104 may determine that it is within the proximity of the access reader 108 in some other manner or may perform the authentication at block 312 in response to some other input.

The wearable electronic device 104 may trigger followup based on the results of the authentication. For instance, the followup may be triggered in response to a negative authentication of the person 102 as the particular user. The followup may be triggered by, e.g., reporting, at block 314, the results of the authentication to the access reader 108, the central monitor server 112, and/or the device server 110.

Alternatively or additionally, the followup may be triggered by the wearable electronic device 104 performing the followup in response to the results of the authentication. In some embodiments, the results of the authentication performed at block 312 may be reported at block 314 without triggering any followup.

At block 316, the followup may be performed based on the reported results (block 314) by the access reader 108, the central monitor server 112, and/or the device server 110 and/or based on the results of the authentication (block 312) by the wearable electronic device itself. As already described, the followup may include sending a notification to a communication address associated with the particular user regarding a negative authentication of the person 102 as the particular user, notifying human security to authenticate the person 102 face to face or visually through a surveillance system, or taking some other action.

The authentication of the person performed at block 312 in FIG. 3A may include at least biometric authentication, which may be combined with token-based authentication (e.g., blocks 304 and 306) in a multifactor authentication as already described. In other embodiments, the multifactor authentication may include knowledge-based authentication instead of or in addition to the token-based authentication. The knowledge-based authentication may be included in the authentication performed at block 312 and/or may include presenting one or more challenge questions to the person and comparing one or more answers to the one or more challenge questions to one or more expected answers, as described elsewhere herein. In these and other embodiments, access to the access-restricted resource 116 may be granted in response to at least one of the factors of the multifactor authentication resulting in a factor-specific positive authentication (e.g., positive knowledge-based, token-based, or biometric-based authentication) and access may be denied in response to each of the factors of the multifactor authentication resulting in negative authentication of the person.

Turning now to FIG. 3B, the method 300B of FIG. 3B may include one or more of blocks 302, 304, 306, 308, 310, 312, 314, and 316 which have already been described with respect to FIG. 3A and which will generally not be described again.

In FIG. 3B, block 306 may be followed by block 308 or block 318. At block 308, access to the access-restricted resource may be denied to the person bearing the wearable electronic device 104. At block 318, it may be determined whether a positive authentication of the person 102 as the particular user was made by the wearable electronic device 314. If not, the method 300B may proceed to block 308 in which access to the access-restricted resource 116 may be denied to the person 102 bearing the wearable electronic device 104. If so, the method 300B may proceed to block 310 in which access to the access-restricted resource 116 may be granted to the person 102 bearing the wearable electronic device.

As described above with respect to FIG. 3A, the authentication of the person performed at block 312 in FIG. 3B may include at least biometric authentication, which may be combined with token-based authentication (e.g., blocks 304 and 306) in a multifactor authentication as already described. In other embodiments, the multifactor authentication may include knowledge-based authentication instead of or in addition to the token-based authentication. The knowledge-based authentication may be included in the authentication performed at block 312 and/or may include presenting one or more challenge questions to the person and comparing one or more answers to the one or more challenge questions to one or more expected answers, as described elsewhere herein. In these and other embodiments, access to the access-restricted resource 116 may be granted in response to each of the factors of the multifactor authentication resulting in a factor-specific positive authentication and access may be denied in response to at least one of the factors of the multifactor authentication resulting in negative authentication of the person.

Turning now to FIG. 3C, the method 300C of FIG. 3C may begin at block 302, in which the wearable electronic device 104 born by the person 102 enters a proximity of the access reader 108. Block 302 may be followed by block 304 (described above but not illustrated in FIG. 3C) and block 320.

At block 320, the wearable electronic device 104, or more particularly, the sensor 208 of the wearable electronic device 104, may generate a biometric signal of the person 102 bearing the wearable electronic device 104. The wearable electronic device 104 may generate the biometric signal in response to determining that the wearable electronic device 104 is within proximity of the access reader 108 as described elsewhere herein, or in response to some other input. Although not illustrated in FIGS. 3A and 3B, the methods 300A and 300B may similarly include the block 320 where the generated biometric signal may be used as an input by the wearable electronic device 104 to perform the authentication at block 312. In FIG. 3C, however, the biometric signal may be sent to the device server 110 where it may be used as an input for the device server 322 to perform the authentication at block 312.

In FIGS. 3A-3C, the authentication performed at block 312 may include biometric authentication such as described in, e.g., U.S. Patent Publication No. 2015/0112603 and/or U.S. Publication No. 2015/0109124. Alternatively or additionally, the authentication performed at block 312 may include biometric authentication as described with respect to FIG. 4 elsewhere herein.

As in FIGS. 3A and 3B, the results of the authentication from block 312 may be reported, although the results may be reported by the device server 110 in the example of FIG. 3C rather than by the wearable electronic device 104. Alternatively or additionally, followup may be performed at block 316 by one or more of the device server 110, the wearable electronic device 104, the access reader 108, and/or the central monitor server 112. Although not illustrated in FIG. 3C, the access reader 108 may perform one or more of blocks 304, 306, 308, and/or 310 as in FIG. 3A to grant or deny access to the access-restricted resource 116 based solely on whether the wearable electronic device 104 is an authorized wearable electronic device 104. Alternatively or additionally, the access reader 108 may perform one or more of blocks 304, 306, 318, 310, and/or 308 as in FIG. 3B to grant or deny access to the access-restricted resource 116 based on both whether the wearable electronic device 104 is an authorized wearable electronic device 104 and whether a positive or negative authentication of the person 102 as the particular user is made.

As described above with respect to FIGS. 3A and 3B, the authentication of the person performed at block 312 in FIG. 3C may include at least biometric authentication, which may be combined with token-based authentication (e.g., blocks 304 and 306 of FIGS. 3A and 3B) in a multifactor authentication as already described. In other embodiments, the multifactor authentication may include knowledge-based authentication instead of or in addition to the token-based authentication. The knowledge-based authentication may be included in the authentication performed at block 312 and/or may include presenting one or more challenge questions to the person and comparing one or more answers to the one or more challenge questions to one or more expected answers, as described elsewhere herein. In these and other embodiments, access to the access-restricted resource 116 may be granted or denied as described with respect to, e.g., FIGS. 3A and 3B.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Moreover, some or all of the functions or blocks described in these and other processes and methods may be implemented by one or more processors executing computer-readable instructions stored on one or more computer-readable media. Execution by the processors of the computer-readable instructions may cause the processors to perform or control performance of the functions or blocks. The processors may include one or more of the processors 202 of FIG. 2 or other processors. The computer-readable media may include one or more of the storage 206 of FIG. 2 or other storage or memory. The computer-readable instructions may include one or more of the access logic 228, the authentication logic 212A, and/or the authentication logic 212B.

Figure 4:
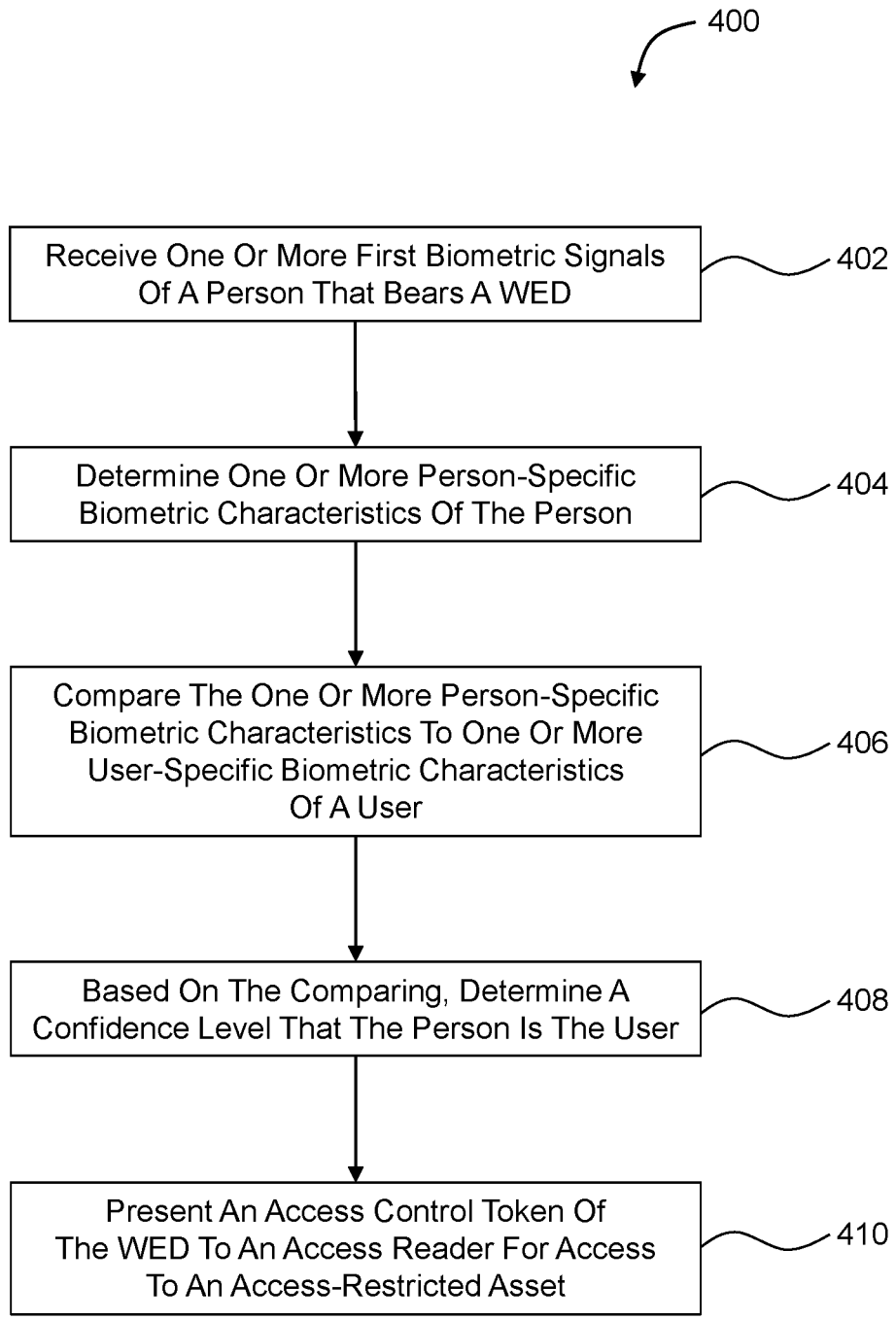
FIG. 4 includes a flow chart of an example method to implement multifactor authentication of a user with a wearable electronic device, all arranged in accordance with at least one embodiment described herein.

FIG. 4 includes a flow chart of an example method 400 to implement multifactor authentication of a user with a wearable electronic device, arranged in accordance with at least one embodiment described herein. The method 400 may include or correspond to block 312 in FIGS. 3A-3C. The method 400 may be implemented, in whole or in part, by the wearable electronic device 104 and/or the device server 110 described elsewhere herein. Alternatively or additionally, execution of the authentication logic 212A by the processor 202A of the wearable electronic device 104 and/or execution of the authentication logic 212B by the processor 202C of the device server 110 may cause the corresponding processor 202A or 202C to perform or control performance of the one or more of the operations or blocks of the method 400. The method 400 may include one or more of blocks 402, 404, 406, 408, and/or 410 and may begin at block 402.

At block 402, one or more first biometric signals of a person that bears a wearable electronic device may be received. The one or more first biometric signals may include, for instance, a first gait signal, a first heart rate signal, or both, or one or more other biometric signals. The one or more first biometric signals may be generated by one or more sensors of the wearable electronic device and may be indicative of one or more person-specific biometric characteristics of a person that bears the wearable electronic device, e.g., at a current time.

At block 404, the one or more person-specific biometric characteristics of the person may be determined from the one or more first biometric characteristics.

At block 406, the one or more person-specific biometric characteristics may be compared to one or more user-specific biometric characteristics of a user determined from one or more second biometric signals generated by the one or more sensors of the wearable electronic device at one or more previous times when the wearable electronic device was born by the user.

At block 408, based on the comparing, a confidence level may be determined that the person is the user to determine a positive authentication or a negative authentication of the person as the user. For instance, in response to the confidence level being above a threshold confidence level, a positive authentication of the person as the user may be made. Alternatively, in response to the confidence level being below the threshold confidence level, a negative authentication of the person as the user may be made.

At block 410, an access control token of the wearable electronic device may be presented to an access reader. The access reader may be configured to grant or deny the person access to an access-restricted resource in response to at least one of the access control token being an authorized access control token or positive or negative authentication of the person as the user. In some embodiments, the access reader may grant or deny the person access to the access-restricted resource as generally described with respect to blocks 304, 306, 308, 310, and/or 318 of FIGS. 3A and 3B.

In some embodiments, and in response to the confidence level being below the threshold confidence level or otherwise making a negative authentication of the person as the user, the method 400 may additionally include causing one or more challenge questions to be presented to the person through the wearable electronic device, a smartphone, or other device or communication medium. In these and other embodiments, a first challenge question may be presented and if the person provides a response that matches an expected response, no other challenge questions may be presented whereas one or more additional challenge questions may be presented if the person fails to provide a response or provides a response that does not match the expected response. During this and other knowledge-based authentication processes, a list of multiple challenge questions may be output to the person and the person may select which one to answer or the person may be unable to choose which of multiple challenge questions to answer and instead may be presented a single challenge question at a time.

In response to receiving one or more answers to the one or more challenge questions that match one or more expected answers to the one or more challenge questions, a positive authentication of the person as the user may be made, or a new confidence level may be calculated based on the previous confidence level and the matching, and the new confidence level may be compared to the threshold confidence level to determine positive or negative authentication of the person as the user. In response to not receiving one or more answers to the one or more challenge questions or in response to receiving one or more answers to the one or more challenge question that do not match the one or more expected answers, a negative authentication of the person as the user may be made, or a new confidence level may be calculated based on the previous confidence level and the matching, and the new confidence level may be compared to the threshold confidence level to determine positive or negative authentication of the person as the user. Results of the biometric and knowledge-based authentication (e.g., the positive and/or negative authentication) may be reported to the access reader.

In other embodiments, and as already described above, the one or more challenge questions with some random or pseudorandom probability or in response to an external indicator may be caused to be presented to the person even if a positive biometric authentication of the person as the user has been made.

In other embodiments, block 410 may be omitted and instead the method 400 may include one or more operations of a knowledge-based authentication. For instance, one or more challenge questions may be presented to the person through the wearable electronic device, a smartphone, or other device or communication medium. In response to receiving one or more answers to the one or more challenge questions that match one or more expected answers to the challenge questions, a positive authentication of the person as the user may be made, or a new confidence level may be calculated based on the previous confidence level and the matching and the new confidence level may be compared to the threshold confidence level to determine positive or negative authentication of the person as the user. In response to not receiving an answer to the one or more challenge questions or in response to receiving one or more answers to the one or more challenge questions that do not match the one or more expected answers, a negative authentication of the person as the user may be made, or a new confidence level may be calculated based on the previous confidence level and the matching and the new confidence level may be compared to the threshold confidence level to determine positive or negative authentication of the person as the user. Results of the biometric and knowledge-based authentication (e.g., the positive or negative authentication) may be reported to the access reader and the access reader may grant or deny access depending thereon.

The method 400 may be combined with one or more of the methods 300 of FIGS. 3A-3C.

Alternatively or additionally, the method may include generating the biometric signature of the user and storing the biometric signature prior to one or more of blocks 402, 404, 406, 408, and/or 410. For instance, the biometric signature may include the one or more user-specific biometric characteristics determined from the one or more second biometric signals. Accordingly, the method 400 may further include receiving the one or more second biometric signals, determining the one or more user-specific biometric characteristics from the one or more second biometric signals, and saving the one or more user-specific biometric characteristics as a biometric signature of the user.

In some embodiments, receiving the one or more first biometric signals generated by the one or more sensors of the wearable electronic device at block 402 may include receiving a first gait signal generated by a gait sensor of the wearable electronic device, the first gait signal indicative of a person-specific gait characteristic of the person that bears the wearable electronic device. Accordingly, determining the one or more person-specific biometric characteristics may include determining the person-specific gait characteristic of the person from the first gait signal. Further, comparing the one or more person-specific biometric characteristics of the person to the one or more user-specific biometric characteristic of the user may include comparing the person-specific gait characteristic of the person to a user-specific gait characteristic of the user determined from a second gait signal generated by the gait sensor of the wearable electronic device at a previous time when the wearable electronic device was born by the user.

Alternatively or additionally, receiving the one or more first biometric signals generated by the one or more sensors of the wearable electronic device may further include receiving a first heart rate signal generated by a heart rate sensor of the wearable electronic device, the first heart rate signal indicative of a person-specific heart rate characteristic of the person that bears the wearable electronic device. Accordingly, determining the one or more person-specific biometric characteristics may further include determining the person-specific heart rate characteristic of the person from the first heart rate signal. Additionally, comparing the one or more person-specific biometric characteristics of the person to the one or more user-specific biometric characteristics of the user may include comparing the person-specific heart rate characteristic of the person to a user-specific heart rate characteristic of the user determined from a second heart rate signal generated by the heart rate sensor of the wearable electronic device at a previous time when the wearable electronic device was born by the user. Finally, based on the comparing, determining the confidence level may include: determining a relatively high confidence level in response to both the person-specific gait characteristic matching the user-specific gait characteristic and the person-specific heart rate characteristic matching the user-specific heart rate characteristic; or determining a relatively lower confidence level in response to either or both of the person-specific gait characteristic not matching the user-specific gait characteristic or the person-specific heart rate characteristic not matching the user-specific heart rate characteristic.

Some biometric sensors used to sense biometric characteristics of a person to biometrically authenticate the person as a user may be expensive and/or stationary, generally being at a fixed location and/or integrated in an access reader. In comparison, some embodiments described herein implement biometric authentication using a relatively inexpensive wearable electronic device which may be less than several hundred U.S. dollars, less than a couple hundred U.S. dollars, or even less than one hundred dollars.

Alternatively or additionally, the authentication performed by the wearable electronic device and/or by the device server may occur without conscious operation of or conscious interaction with the wearable electronic device by the person that bears the wearable electronic device. In these and other embodiments, the one or more biometric signals from which the one or more biometric characteristics are determined may be generated continuously or semi-continuously and may be stored, in whole or in part, locally on the wearable electronic device and/or remotely on the device server. When the authentication is performed, the wearable electronic device and/or the device server may determine the one or more biometric characteristics from a most recent portion of the one or more biometric signals defined in terms of samples, time, or some other parameter. This may speed up the authentication process compared to more conventional authentication processes in which a person arrives at a biometric sensor that by itself or together with an access reader controls access to an access-restricted resource and the person has to consciously interact with a biometric sensor (e.g., fingerpint scanner, retinal scanner) to collect a biometric signal before authentication can begin. In comparison, according to embodiments described herein, the one or more biometric signals may have already been generated and received by the time the person arrives at the access reader, at which point the authentication can begin immediately without waiting to collect further biometric signals.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method to implement multifactor authentication of a user with a wearable electronic device of the user, the method comprising:
    performing biometric authentication of a person that bears the wearable electronic device, including:
        receiving one or more first biometric signals generated by one or more sensors of the wearable electronic device, the one or more first biometric signals indicative of one or more person-specific biometric characteristics of the person;
        determining the one or more person-specific biometric characteristic of the person from the one or more first biometric signals;
        comparing the one or more person-specific biometric characteristics to one or more user-specific biometric characteristics of the user determined from one or more second biometric signals generated by the one or more sensors of the wearable electronic device at one or more previous times when the wearable electronic device was borne by the user; and
        based on the comparing, determining a confidence level that the person is the user to determine a positive or negative biometric authentication of the person as the user;
    presenting an access control token of the wearable electronic device to an access reader that performs token-based authentication of the person, wherein the access control token presented to the access reader is an authorized access control token and the access reader is configured to grant the person access to an access-restricted resource based solely on the access control token being an authorized access control token;
    in response to the confidence level being below a threshold confidence level, causing a challenge question to be presented to the person;
    making a positive authentication of the person as the user in response to receiving an answer to the challenge question that matches an expected answer to the challenge question;
    making a negative authentication of the person as the user in response to not receiving an answer to the challenge question or in response to receiving an answer to the challenge question that does not match the expected answer;
    granting the person access to the access-restricted resource based on the access control token being an authorized access control token even when a negative authentication based on biometric authentication and/or knowledge based authentication occurs; and
    in response to the negative authentication, triggering a followup that would not be triggered absent the negative authentication.

2. A method to implement multifactor authentication of a user with a wearable electronic device of the user, the method comprising:
    performing biometric authentication of a person that bears the wearable electronic device, including:
        receiving one or more first biometric signals generated by one or more sensors of the wearable electronic device, the one or more first biometric signals indicative of one or more person-specific biometric characteristics of the person;
        determining the one or more person-specific biometric characteristic of the person from the one or more first biometric signals;
        comparing the one or more person-specific biometric characteristics to one or more user-specific biometric characteristics of the user determined from one or more second biometric signals generated by the one or more sensors of the wearable electronic device at one or more previous times when the wearable electronic device was borne by the user; and
        based on the comparing, determining a confidence level that the person is the user to determine a positive or negative biometric authentication of the person as the user;
    presenting an access control token of the wearable electronic device to an access reader that performs token-based authentication of the person, wherein the access control token presented to the access reader is an authorized access control token and the access reader is configured to grant the person access to the access-restricted resource based solely on the access control token being the authorized access control token;
    granting the person access to the access-restricted resource based on the access control token being the authorized access control token even when a negative biometric authentication of the person as the user occurs; and
    in response to negative biometric authentication of the person as the user based on the confidence level being below a threshold confidence level, triggering a followup that would not be triggered in response to positive biometric authentication of the person as the user.

3. The method of claim 2, wherein triggering the followup comprises reporting the negative biometric authentication to at least one of the access reader or a server to cause:
    the at least one of the access reader or the server to send a notification regarding the negative authentication to a communication address associated with the user; or
    the at least one of the access reader or the server to notify human security to authenticate the person face to face or visually through a surveillance system.

4. The method of claim 1, wherein triggering the followup comprises reporting the negative authentication to at least one of the access reader or a server to cause:
    the at least one of the access reader or the server to send a notification regarding the negative authentication to a communication address associated with the user; or the at least one of the access reader or the server to notify human security to authenticate the person face to face or visually through a surveillance system.

5. The method of claim 1, wherein:
receiving the one or more first biometric signals generated by the one or more sensors of the wearable electronic device comprises receiving a first gait signal generated by a gait sensor of the wearable electronic device, the first gait signal indicative of a person-specific gait characteristic of the person that bears the wearable electronic device;
determining the one or more person-specific biometric characteristics comprises determining the person-specific gait characteristic of the person from the first gait signal; and
comparing the one or more person-specific biometric characteristics of the person to the one or more user-specific biometric characteristic of the user comprises comparing the person-specific gait characteristic of the person to a user-specific gait characteristic of the user determined from a second gait signal generated by the gait sensor of the wearable electronic device at a previous time when the wearable electronic device was borne by the user.

6. The method of claim 5, wherein:
receiving the one or more first biometric signals generated by the one or more sensors of the wearable electronic device further comprises receiving a first heart rate signal generated by a heart rate sensor of the wearable electronic device, the first heart rate signal indicative of a person-specific heart rate characteristic of the person that bears the wearable electronic device;
determining the one or more person-specific biometric characteristics further comprises determining the person-specific heart rate characteristic of the person from the first heart rate signal;
comparing the one or more person-specific biometric characteristics of the person to the one or more user-specific biometric characteristic of the user comprises comparing the person-specific heart rate characteristic of the person to a user-specific heart rate characteristic of the user determined from a second heart rate signal generated by the heart rate sensor of the wearable electronic device at a previous time when the wearable electronic device was borne by the user; and
based on the comparing, determining the confidence level comprises:
determining a relatively high confidence level in response to both the person-specific gait characteristic matching the user-specific gait characteristic and the person-specific heart rate characteristic matching the user-specific heart rate characteristic; or
determining a relatively lower confidence level in response to either or both of the person-specific gait characteristic not matching the user-specific gait characteristic or the person-specific heart rate characteristic not matching the user-specific heart rate characteristic.

7. The method of claim 1, wherein the receiving, the determining the person-specific biometric characteristic, the comparing, and the determining the confidence level all occur without conscious operation of or conscious interaction with the wearable electronic device by the person that bears the wearable electronic device.

8. The method of claim 1, further comprising presenting one or more challenge questions to the person using random probability after making a positive biometric authentication of the person as the user.

9. A non-transitory computer-readable medium having computer-executable instructions stored thereon that are executable by a processor to perform or control performance of operations to implement multifactor authentication of a user with a wearable electronic device of the user, the operations comprising:
performing biometric authentication of a person that bears the wearable electronic device, including:
receiving one or more first biometric signals generated by one or more sensors of the wearable electronic device, the one or more first biometric signals indicative of one or more person-specific biometric characteristics of the person;
determining the one or more person-specific biometric characteristic of the person from the one or more first biometric signals;
comparing the one or more person-specific biometric characteristics to one or more user-specific biometric characteristics of the user determined from one or more second biometric signals generated by the one or more sensors of the wearable electronic device at one or more previous times when the wearable electronic device was borne by the user; and
based on the comparing, determining a confidence level that the person is the user to determine a positive or negative authentication of the person as the user;
presenting an access control token of the wearable electronic device to an access reader that performs token-based authentication of the person, wherein the access control token presented to the access reader is an authorized access control token and the access reader is configured to grant the person access to an access-restricted resource based solely on the access control token being an authorized access control token;
in response to the confidence level being below a threshold confidence level, causing a challenge question to be presented to the person;
making a positive authentication of the person as the user in response to receiving an answer to the challenge question that matches an expected answer to the challenge question;
making a negative authentication of the person as the user in response to not receiving an answer to the challenge question or in response to receiving an answer to the challenge question that does not match the expected answer;
granting the person access to the access-restricted resource based on the access control token being an authorized access control token even when a negative authentication based on biometric authentication and/or knowledge based authentication occurs; and
in response to the negative authentication, triggering a followup that would not be triggered absent the negative authentication.

10. The non-transitory computer-readable medium of claim 9, wherein triggering the followup comprises reporting the negative authentication to at least one of the access reader or a central monitor server to cause:
the at least one of the access reader or the central monitor server to send a notification regarding the negative authentication to a communication address associated with the user; or the at least one of the access reader or the central monitor server to notify human security to authenticate the person face to face or visually through a surveillance system.

11. The non-transitory computer-readable medium of claim 9, wherein the receiving, the determining the person-specific biometric characteristic, the comparing, and the determining the confidence level all occur without conscious operation of or conscious interaction with the wearable electronic device by the person that bears the wearable electronic device.

12. The non-transitory computer-readable medium of claim 9, the operations further comprising presenting one or more challenge questions to the person using random probability after making a positive biometric authentication of the person as the user.

13. A wearable electronic device, comprising:
an access control token presentable to an access reader;
one or more sensors configured to generate one or more first biometric signals indicative of one or more person-specific biometric characteristics of a person that bears the wearable electronic device at a first time and one or more second biometric signals indicative of one or more user-specific biometric characteristics of a user at one or more times prior to the first time and when a user associated with the wearable electronic device bears the wearable electronic device;
a non-transitory computer-readable medium configured to store therein authentication logic; and
a processor configured to execute the authentication logic to perform or control performance of operations comprising:
determining the one or more person-specific biometric characteristic from the one or more first biometric signals;
determining the one or more user-specific biometric characteristic from the one or more second biometric signals;
comparing the one or more person-specific biometric characteristics to the one or more user-specific biometric characteristics; and
based on the comparing, determining a confidence level that the person is the user to determine a positive or negative authentication of the person as the user;
presenting the access control token of the wearable electronic device to the access reader that performs token-based authentication of the person, wherein the access control token is an authorized access control token and wherein the access reader is configured to grant the person access to an access-restricted resource based solely on the access control token being an authorized access control token;
in response to the confidence level being below a threshold confidence level, the wearable device causing a challenge question to be presented to the person;
making a positive authentication of the person as the user in response to receiving an answer to the challenge question that matches an expected answer to the challenge question;
making a negative authentication of the person as the user in response to not receiving an answer to the challenge question or in response to receiving an answer to the challenge question that does not match the expected answer;
granting the person access to the access-restricted resource based on the access control token being an authorized access control token even when a negative authentication based on biometric authentication and/or knowledge based authentication occurs; and
in response to the negative authentication, triggering a followup that would not be triggered absent the negative authentication.

14. The wearable electronic device of claim 13, wherein the one or more sensors include a gait sensor and a heart rate sensor.

15. The method of claim 1, wherein causing the challenge question to be presented to the person comprises the wearable electronic device causing the challenge question to be presented to the person.

16. The method of claim 15, wherein the wearable electronic device causing the challenge question to be presented to the person comprises the wearable electronic device causing the challenge question to be presented to the person through the wearable electronic device.

17. The method of claim 15, wherein the wearable electronic device causing the challenge question to be presented to the person comprises the wearable electronic device causing the challenge question to be presented to the person through a phone of the person.

18. The method of claim 2, wherein causing the challenge question to be presented to the person comprises the wearable electronic device causing the challenge question to be presented to the person.

19. The method of claim 2, wherein:
receiving the one or more first biometric signals generated by the one or more sensors of the wearable electronic device comprises receiving a first gait signal generated by a gait sensor of the wearable electronic device, the first gait signal indicative of a person-specific gait characteristic of the person that bears the wearable electronic device;
determining the one or more person-specific biometric characteristics comprises determining the person-specific gait characteristic of the person from the first gait signal; and
comparing the one or more person-specific biometric characteristics of the person to the one or more user-specific biometric characteristic of the user comprises comparing the person-specific gait characteristic of the person to a user-specific gait characteristic of the user determined from a second gait signal generated by the gait sensor of the wearable electronic device at a previous time when the wearable electronic device was borne by the user.

20. The method of claim 19, wherein:
receiving the one or more first biometric signals generated by the one or more sensors of the wearable electronic device further comprises receiving a first heart rate signal generated by a heart rate sensor of the wearable electronic device, the first heart rate signal indicative of a person-specific heart rate characteristic of the person that bears the wearable electronic device;
determining the one or more person-specific biometric characteristics further comprises determining the person-specific heart rate characteristic of the person from the first heart rate signal;
comparing the one or more person-specific biometric characteristics of the person to the one or more user-specific biometric characteristic of the user comprises comparing the person-specific heart rate characteristic of the person to a user-specific heart rate characteristic of the user determined from a second heart rate signal generated by the heart rate sensor of the wearable electronic device at a previous time when the wearable electronic device was borne by the user; and based on the comparing, determining the confidence level comprises:

determining a relatively high confidence level in response to both the person-specific gait characteristic matching the user-specific gait characteristic and the person-specific heart rate characteristic matching the user-specific heart rate characteristic; or determining a relatively lower confidence level in response to either or both of the person-specific gait characteristic not matching the user-specific gait characteristic or the person-specific heart rate characteristic not matching the user-specific heart rate characteristic.

21. The non-transitory computer-readable medium of claim 9, wherein causing the challenge question to be presented to the person comprises the wearable electronic device causing the challenge question to be presented to the person.

22. The non-transitory computer-readable medium of claim 9, wherein:

receiving the one or more first biometric signals generated by the one or more sensors of the wearable electronic device comprises receiving a first gait signal generated by a gait sensor of the wearable electronic device, the first gait signal indicative of a person-specific gait characteristic of the person that bears the wearable electronic device;

determining the one or more person-specific biometric characteristics comprises determining the person-specific gait characteristic of the person from the first gait signal; and comparing the one or more person-specific biometric characteristics of the person to the one or more user-specific biometric characteristic of the user comprises comparing the person-specific gait characteristic of the person to a user-specific gait characteristic of the user determined from a second gait signal generated by the gait sensor of the wearable electronic device at a previous time when the wearable electronic device was borne by the user.

23. The non-transitory computer-readable medium of claim 22, wherein:

receiving the one or more first biometric signals generated by the one or more sensors of the wearable electronic device further comprises receiving a first heart rate signal generated by a heart rate sensor of the wearable electronic device, the first heart rate signal indicative of a person-specific heart rate characteristic of the person that bears the wearable electronic device;

determining the one or more person-specific biometric characteristics further comprises determining the person-specific heart rate characteristic of the person from the first heart rate signal;

comparing the one or more person-specific biometric characteristics of the person to the one or more user-specific biometric characteristic of the user comprises comparing the person-specific heart rate characteristic of the person to a user-specific heart rate characteristic of the user determined from a second heart rate signal generated by the heart rate sensor of the wearable electronic device at a previous time when the wearable electronic device was borne by the user; and based on the comparing, determining the confidence level comprises:

determining a relatively high confidence level in response to both the person-specific gait characteristic matching the user-specific gait characteristic and the person-specific heart rate characteristic matching the user-specific heart rate characteristic; or determining a relatively lower confidence level in response to either or both of the person-specific gait characteristic not matching the user-specific gait characteristic or the person-specific heart rate characteristic not matching the user-specific heart rate characteristic.

* * * * *